(12) United States Patent
Kreindel

(10) Patent No.: US 11,653,971 B2
(45) Date of Patent: May 23, 2023

(54) RF DEVICE FOR TISSUE TREATMENT

(71) Applicant: Inmode Ltd., Yokneam (IL)

(72) Inventor: Michael Kreindel, Richmond Hill (CA)

(73) Assignee: Inmode Ltd., Yokneam (IL)

( * ) Notice: Subject to any disclaimer, the term of this patent is extended or adjusted under 35 U.S.C. 154(b) by 201 days.

(21) Appl. No.: 16/810,874

(22) Filed: Mar. 6, 2020

(65) Prior Publication Data

US 2020/0281642 A1    Sep. 10, 2020

Related U.S. Application Data

(60) Provisional application No. 62/816,134, filed on Mar. 10, 2019.

(51) Int. Cl.
*A61B 18/14*    (2006.01)
*A61B 18/12*    (2006.01)
*A61B 18/00*    (2006.01)

(52) U.S. Cl.
CPC ........ *A61B 18/148* (2013.01); *A61B 18/1206* (2013.01); *A61B 2018/0047* (2013.01); *A61B 2018/0091* (2013.01); *A61B 2018/00452* (2013.01); *A61B 2018/00791* (2013.01); *A61B 2018/126* (2013.01); *A61B 2018/1253* (2013.01); *A61B 2018/142* (2013.01)

(58) Field of Classification Search
CPC ... A61B 18/1206; A61B 18/14; A61B 18/148; A61B 18/00702; A61B 18/00791; A61B 2018/00321; A61B 2018/00452; A61B 2018/00458; A61B 2018/00464; A61B 2018/0047; A61B 2018/00702; A61B 2018/0091; A61B 2018/126; A61B 2018/142

See application file for complete search history.

(56) References Cited

U.S. PATENT DOCUMENTS

| 2009/0018628 | A1* | 1/2009 | Burns | A61B 18/14 |
| | | | | 607/101 |
| 2010/0210993 | A1* | 8/2010 | Flyash | A61N 1/36034 |
| | | | | 604/20 |

* cited by examiner

*Primary Examiner* — Michael F Peffley
*Assistant Examiner* — Samantha M Good
(74) *Attorney, Agent, or Firm* — Dekel Patent Ltd.; David Klein

(57) ABSTRACT

An applicator includes at least one RF electrode coupled to an RF generator. The at least one RF electrode has protrusions each with a curvature radius which is equal to or greater than a curvature radius of an outer edge of the at least one RF electrode.

6 Claims, 5 Drawing Sheets

RF DEVICE FOR TISSUE TREATMENT

FIELD OF THE INVENTION

The invention relates to a method of treatment using radio-frequency (RF) energy for non-ablative treatment of skin without hot spots.

BACKGROUND OF THE INVENTION

RF devices for non-ablative treatment are commonplace in medical aesthetic practice. The devices are differentiated by the type of energy application.

Some of the treatments are based on moving a hand piece over the skin surface and delivering RF energy continuously. The treatment effect is achieved by elevating skin temperature during multiple passes. RF energy is delivered in continuous mode and the hand piece is moved over the treated area to reach a skin target temperature and maintain it for a required time.

The other broadly used treatment option is the application of all the energy required for the treatment effect to one spot and then moving the hand piece to a new spot. Bi-polar and mono-polar RF devices are used for this type of treatment.

Typically, the tissue is heated to 40-50° C. and maintained at this temperature over a period of time, such as from a few minutes up to 30 minutes. Skin temperature can be monitored to optimize the treatment.

Treatment results are a function of the heating level which is limited by safety and comfort level and the time that heating is maintained. Long treatment is annoying for the treatment attendant and expensive for the patient.

One of the problems in the prior art is hot spots can occur at the edges of the RF electrode. The hot spots are a result of high electric fields at the higher curvature of the electrode at the edge. The triple contact point between electrode, air and tissue results in higher RF current density. Using electrodes with rounded edges and applying conductive gel or liquid around the contact reduces hot spots but not completely.

SUMMARY OF THE INVENTION

The present invention is a design of RF electrodes for non-ablative thermal medical or cosmetic treatment with improved RF energy uniformity over the electrode area. The invention uses an electrode with a highly curved surface, creating multiple overlapped hot zones which diminish the edge effect. The shapes of irregularities covering the electrode surface are high enough to create RF current density similar to the density on the electrode edge. The density of irregularities is high enough to create overlapping of hot zones, which results in virtually uniform heating under all areas of the RF electrode. The method is applicable for heating large volumes of tissue to sub-necrotic level to avoid overheating (overheating by a few degrees may result in tissue damage). This type of treatment is typical for treatment of periorbital, peri-oral and other wrinkles, tissue tightening, fat reduction and other types of tissue remodeling.

This method is not applicable for cutting electrosurgical tools where the edge effect is used for focusing RF current at a small area to create tissue ablation.

This method can be applied to the monopolar or bipolar RF devices used in the aesthetics or medicine. The hand piece applied to the patient tissue may have one, two or more electrodes designed according to the invention.

For a long thin electrode, the protruding element may have a linear shape parallel to the electrode's long side. Alternatively, bulge or pin type protruding elements can be spread over the area of the electrode.

The protrusions over the electrode area can have the same shape or can have variable curvature to create more uniform thermal profile.

In order to improve contact between the shaped electrode and tissue, a conductive gel can be used for electrical coupling.

Tissue impedance and RF parameters can be monitored by the system and RF energy can be adjusted according to measurements. If measured impedance is out of an accepted range, the RF energy can be stopped.

The temperature sensor can be embedded into the hand piece to control the skin heating process. RF energy can be adjusted according to feedback from the temperature sensor. The temperature sensor can be a thermistor, thermocouple, optical sensors or other.

The electrode should be large enough to implement the current invention. The contact area with the skin may be in the range of 6 $mm^2$ to 20 $cm^2$ for treatment tissue area of 1 $cm^2$ and larger.

The tissue applicator with electrodes is connected to the radio-frequency generator. The typical average RF power is in the range of 1 W up to 400 W. RF energy can be delivered in pulse, continuous mode or in a train of pulses. RF energy can be reduced when the target temperature is approached. RF energy can be switched on and off to maintain target temperature. The treatment time can be varied, without limitation, from 1 min and up to 30 min.

The target temperature can be varied, without limitation, from 40° C. up to 50° C. RF frequency may be, without limitation, in the range of 100 kHz up to 40 MHz. The preferable range is 400 kHz to 6 MHz.

DETAILED DESCRIPTION

Figure 1:
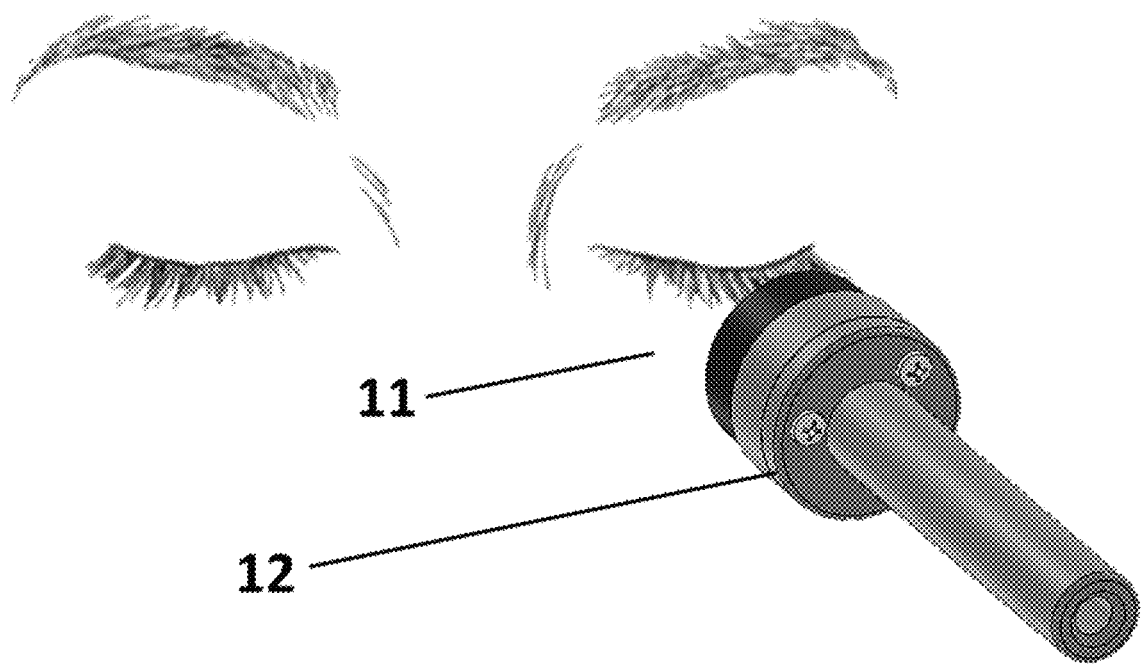
FIG. 1 is a schematic representation of the hand piece applied for treatment of peri-orbital wrinkles.

Referring first to FIG. 1, a device 12 is applied to the lower eyelid 11 for treatment of peri-orbital wrinkles. Alternatively other areas outside of the face or body can be treated. The device can be used for treatment inside the natural openings.

Figure 2:
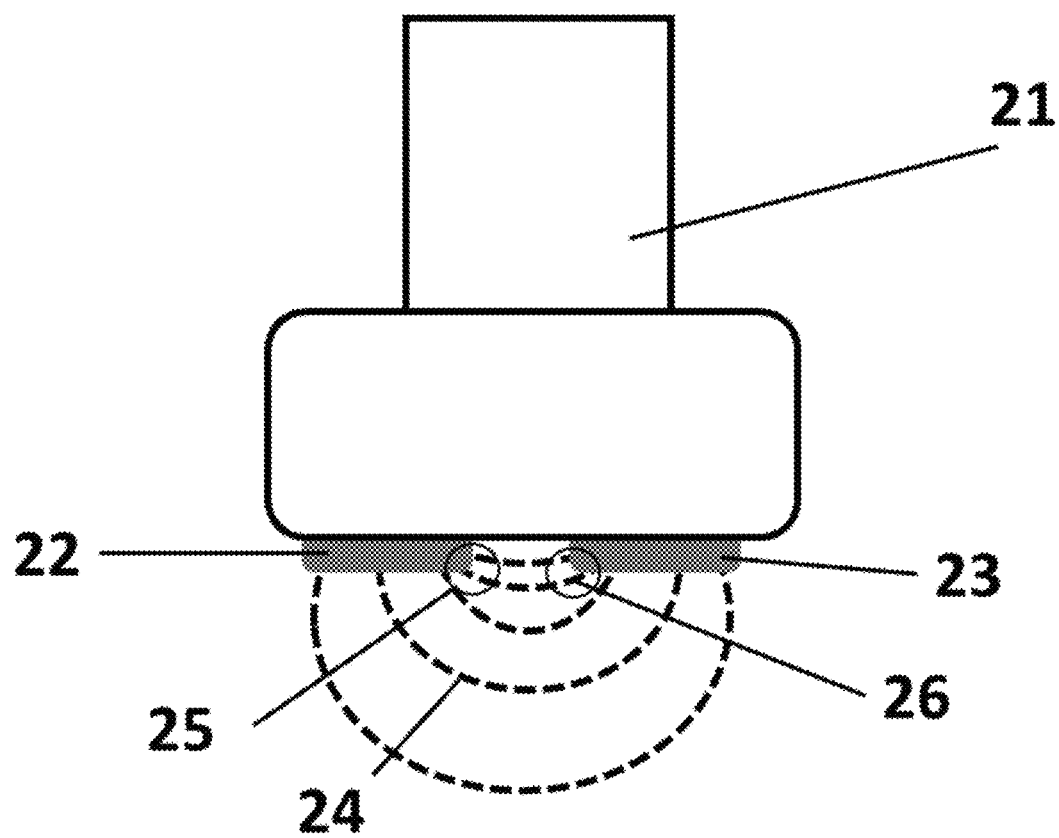
FIG. 2 is a schematic representation of the RF current distribution between two smooth electrodes.

FIG. 2 shows the distribution of RF current 24 between two electrodes 22 and 23 connected to hand piece 21. RF current 24 has a higher density near the inner edges of the electrodes 22, 23 creating hot spots 25, 26. These hot spots can result in thermal damage of the tissue.

Figure 3:
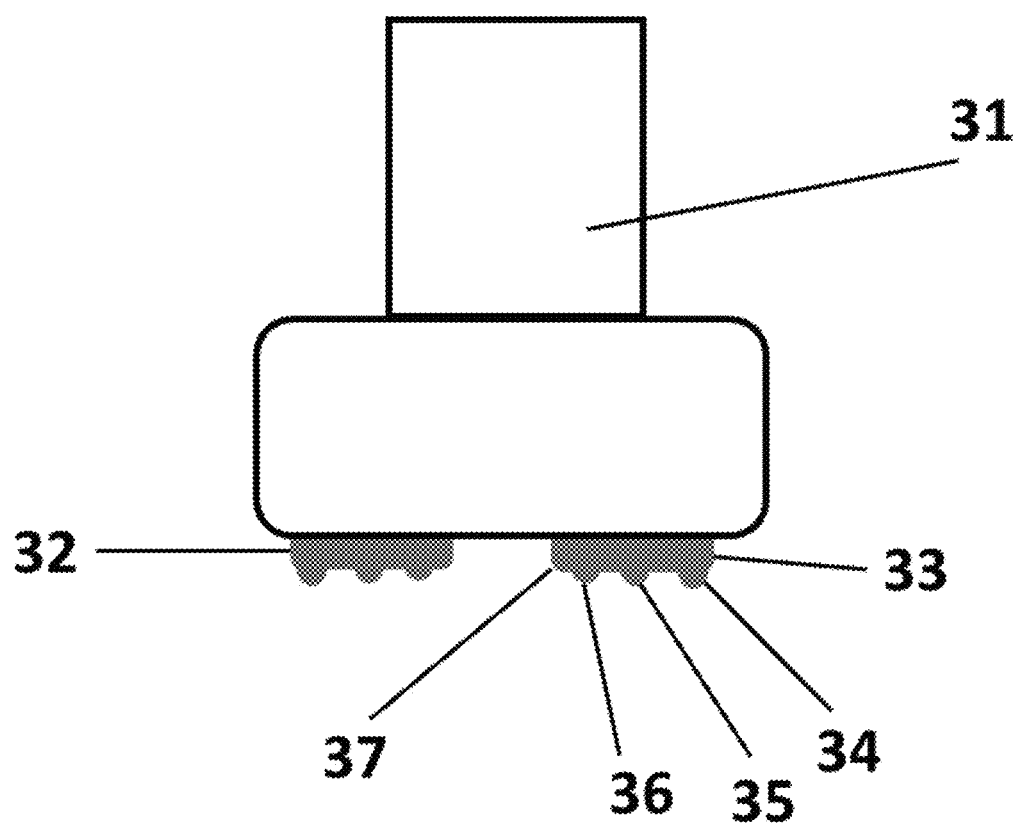
FIG. 3 is a schematic representation of the hand piece with RF two electrodes having protrusions.

FIG. 3 shows hand piece 31 according to an embodiment of the invention with two electrodes 32, 33 applied to the treated tissue. Each electrode has an internal edge 37 and protrusions 34, 35, and 36.

Figure 4:
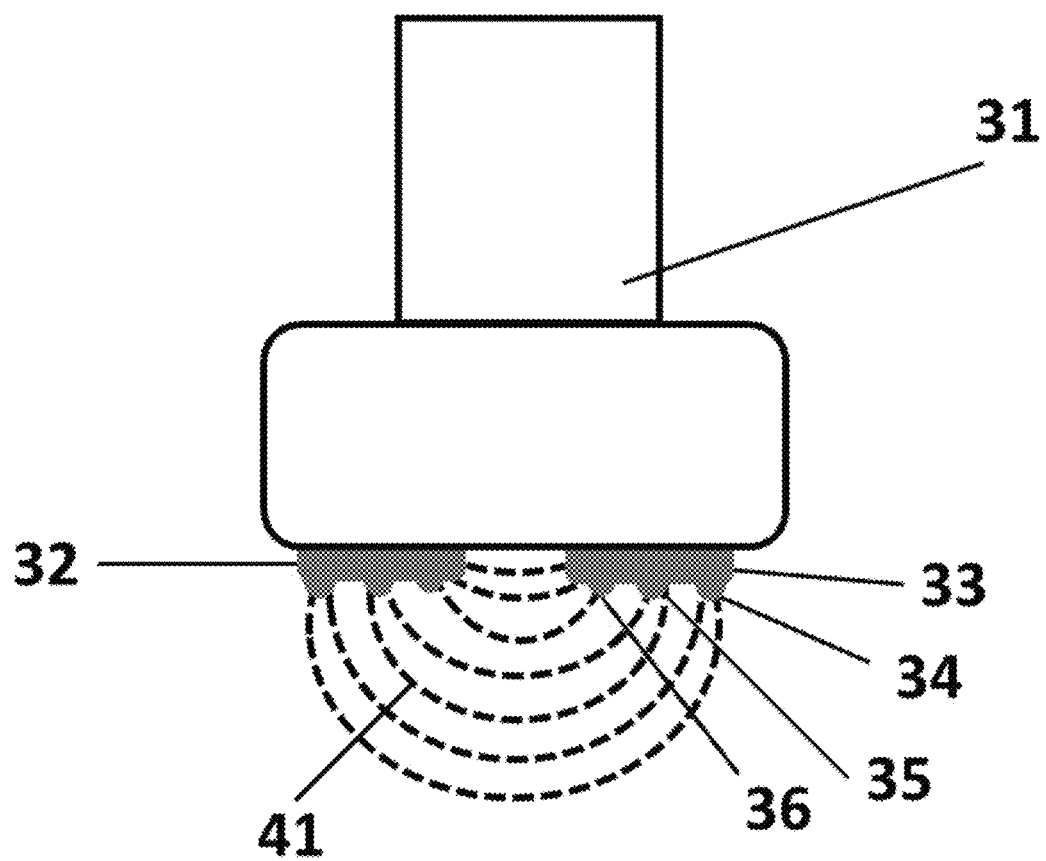
FIG. 4 is a schematic representation of the RF current distribution between two electrodes with protrusions.

FIG. 4 shows hand piece 31 according to an embodiment of the invention with two electrodes 32, 33 applied to the treated tissue. Each electrode has protrusions 34, 35, and 36. The RF current 41 concentrated on protrusions in the same way as on the inner edge of electrodes, creating a more uniform RF current distribution over the electrode area in comparison with smooth electrodes shown in FIG. 2.

Figure 5:
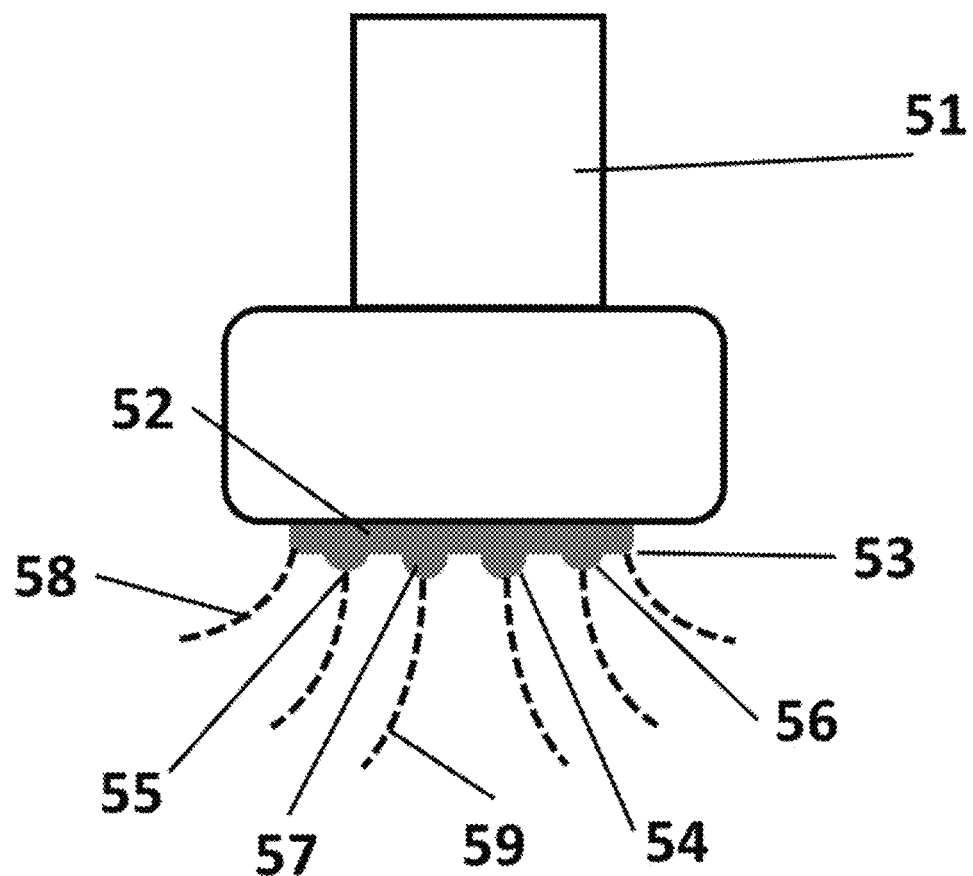
FIG. 5 is a schematic representation of the RF current distribution at mono-polar electrode with protrusions.

FIG. 5 shows mono-polar hand piece 51 according to an embodiment of the invention with single electrodes 52 applied to the treated tissue. Each electrode has an inner edge 53 and protrusions 54, 55, 56, and 57.

The hand piece is connected to the RF generator generating electrical current with a frequency, without limitation, of 400 kHz to 6 MHz. Electrodes 52 have an embedded thermal sensor monitoring skin temperature during the treatment.

FIG. 5 shows the hand piece surface with two electrodes 52. The electrode has edge 53 and protrusions 54-57. The protrusions amplify RF current density 59 in the inner part of electrode to make it virtually equal to the current density 58 at the edge of electrode.

The treatment with the RF device having electrodes according to the invention, without limitation, has the following steps:
  Applying layer of conductive gel which thick enough to fill volume in between protrusions
  Applying hand piece to the treated tissue with firm pressure to ensure good contact between skin and electrodes.
  Move hand piece over the treatment area to reach and maintain skin temperature in the range of 40° C. to 50° C. RF energy is terminated when skin temperature reaches the pre-set level and turned on automatically when measured temperature is below the pre-set level.

The preferred parameters for device, without limitation, are the following:
  1. RF peak voltage applied to the tissue in the range of 10V to 1000V
  2. Average RF power from 1 W to 50 W
  3. RF frequency in the range of 400 kHz to 6 MHz
  4. Tissue contacting area of hand piece is 0.1 $cm^2$ to 6 $cm^2$
  5. Temperature sensor embedded into the one or more electrodes controls maximal tissue heating in the range of 40° C. to 50° C. according to user setting.
  6. RF energy as controlled according to feedback from temperature sensor and impedance measurements. If measured parameters are out of accepted range, the RF energy is terminated.

The invention claimed is:

1. A device for non-ablative thermal treatment of tissue comprising:
   an RF (radio frequency) generator; and
   an applicator comprising at least one RF electrode coupled to said RF generator, wherein said at least one RF electrode comprises an array of spaced-apart protrusions located on a distal face of said at least one RF electrode, said protrusions extending between inner and outer portions of said at least one RF electrode, and each of said protrusions having a curved distal tip being defined by a radius of curvature and an amount of protrusion from said distal face, and wherein said radii of curvature or said amounts of protrusion vary between said inner and said outer portions of said at least one RF electrode.

2. The device according to claim 1, further comprising a tissue temperature sensor coupled to said applicator.

3. The device according to claim 2, wherein RF energy is adjusted according to tissue temperature monitored by said tissue temperature sensor.

4. The device according to claim 1, wherein said at least one RF electrode has a contact area larger than 6 $mm^2$.

5. The device according to claim 1, wherein some of said radii of curvature or said amounts of protrusion increase from said inner to said outer portions of said at least one RF electrode.

6. The device according to claim 1, wherein some of said radii of curvature or said amounts of protrusion decrease from said inner to said outer portions of said at least one RF electrode.

* * * * *